United States Patent [19]
Gaffar et al.

[11] 4,137,303
[45] Jan. 30, 1979

[54] ANTIBACTERIAL ORAL COMPOSITION

[75] Inventors: Abdul Gaffar; Anthony R. Volpe, both of Somerset, N.J.

[73] Assignee: Colgate Palmolive Company, New York, N.Y.

[21] Appl. No.: 803,084

[22] Filed: Jun. 3, 1977

Related U.S. Application Data

[63] Continuation-in-part of Ser. No. 588,094, Jun. 18, 1975, abandoned.

[51] Int. Cl.$^2$ .................... A61K 7/16; A61K 7/18; A61K 7/22
[52] U.S. Cl. ................................ 424/52; 424/54
[58] Field of Search ........................... 424/54, 52

[56] References Cited

U.S. PATENT DOCUMENTS 3,934,002  1/1976  Haefele ............................ 424/54

FOREIGN PATENT DOCUMENTS 2159507  7/1973  France.

OTHER PUBLICATIONS

Chem. Abstracts 80 #30710a(1974) of Crutchfield et al. Fr. Demande 2,159,507 27 Jul. 1973, 12 pp., "Tartar-Retarding Toothpastes Containing Polyamine Polyphosphonates".
Chem. Abstracts 84 #111684e(1976) of Haefele U.S. 3,934,002 20 Jan. 1976, "Oral Compositions for Plaque Caries and Calculus Retardation with Reduced Staining Tendencies".

*Primary Examiner*—Shep K. Rose
*Attorney, Agent, or Firm*—Robert L. Stone; Murray M. Grill; Herbert S. Sylvester

[57] ABSTRACT

An antibacterial oral composition effective to promote oral hygiene containing an antibacterial antiplaque agent and an additive which reduces staining of dental surfaces caused by the antibacterial antiplaque agent without substantially diminishing the antibacterial and antiplaque activity of the agent. Bis-biguanido hexanes, such as chlorhexidine and alexidine, and quaternary ammonium salts, such as benzethonium chloride and cetyl pyridinium chloride, are typical examples of antibacterial agents. The stain reduction additive is a polyamine polyphosphonic compound, such as ethylenediamine tetra(methylene phosphonic acid) and salts thereof.

23 Claims, No Drawings

ANTIBACTERIAL ORAL COMPOSITION

This application is a continuation-in-part of Ser. No. 588,094, filed June 18, 1975, now abandoned.

This invention relates to an antibacterial oral composition which promotes oral hygiene.

Cationic antibacterial materials are well known in the art. See, for instance the section on "Quaternary Ammonium and Related Compounds" in the article on "Antiseptics and Disinfectants" in Kirk-Othmer Encyclopedia of Chemical Technology 2nd edition (Vol. 2, p. 632–635), incorporated herein by reference. Cationic materials which possess antibacterial activity (i.e. are germicides) are used against bacteria. As bacteria are present in the oral cavity and lead to plaque formation, cationic antibacterial agents have been used in oral compositions to counter plaque formation.

Among the most common of these antibacterial antiplaque quaternary ammonium compounds is benzethonium chloride, also known as Hyamine 1622 or di-iso butyl phenoxyethoxyethyl dimethyl benzyl ammonium chloride. In an oral preparation this material is highly effective in promoting oral hygiene by reducing formation of dental plaque and calculus. Reduction of plaque and calculus is generally accompanied by reduction in caries formation. Other cationic antibacterial agents of this type are those mentioned, for instance, in U.S. Pat. Nos. 2,984,639; 3,325,402; 3,703,583; and 3,431,208 and British Pat. No. 1,319,396.

Other antibacterial antiplaque quaternary ammonium compounds include those in which one or two of the substituents on the quaternary nitrogen has a carbon chain length (typically alkyl group) of some 8 to 20, typically 10 to 18, carbon atoms while the remaining substituents have a lower number of carbon atoms (typically alkyl or benzyl group), such as 1 to 7 carbon atoms, typically methyl or ethyl groups. Dodecyl trimethyl ammonium bromide, benzyl dimethyl stearyl ammonium chloride, cetyl pyridinium chloride and quaternized 5amino-1,3-bis (2-ethylhexyl)-5-methyl hexa hydro-pyrimidine are typical quaternary ammonium antibacterial agents.

Other types of cationic antibacterial agents which are desirably incorporated in oral compositions to promote oral hygiene by reducing plaque formation are the amidines such as the substituted guanidines e.g. chlorhexidine and the corresponding compound, alexidine, having 2-ethylhexyl groups instead of chlorophenyl groups and other bis-biguanides such as those described in German patent application P 2,332,383 published Jan. 10, 1974, which sets forth the following formula:

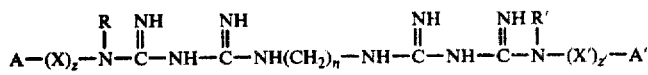

in which A and A' signify as the case may be either (1) a phenyl radical, which as substituent can contain up to 2 alkyl or alkoxy groups with 1 up to about 4C-atoms, a nitro group or a halogen atom, (2) an alkyl group which contains 1 to about 12 C-atoms, or (3) alicyclic groups with 4 to about 12C-atoms, X and X' as the case may be may represent an alkylene radical with 1-3C-atoms, z and z' are as the case may be either zero or 1, R and R' as the case may be may represent either hydrogen, an alkyl radical with 1 to about 12C-atoms or an aralkyl radical with 7 to about 12C-atoms n is a whole number of 2 to inclusively 12 and the polymethylene chain $(CH_2)_n$ can be interrupted by up to 5 ether, thioether, phenyl- or naphthyl groups; these are available as pharmaceutically suitable salts. Additional substituted guanidines are: N'-(4-chlorobenzyl)-N$^5$-(2,4-dichlorobenzyl) biguanide; p-chlorobenzyl biguanide, 4-chlorobenzhydryl guanylurea; N-3-lauroxypropyl-N$^5$-p-chlorobenzyl biguanide; 5,6-dichloro-2-guanidobenzimidazole; and N-p-chlorophenyl-N$^5$-laurylbiguanide.

The long chain tertiary amines also possess antibacterial and antiplaque activity. Such antibacterial agents include tertiary amines having one fatty alkyl group (typically 12 to 18 carbon atoms) and 2 poly(oxyethylene) groups attached to the nitrogen (typically containing a total of from 2 to 50 ethenoxy groups per molecule) and salts thereof with acids and compounds of the structure:

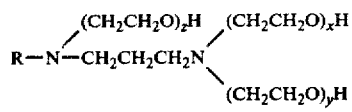

wherein R is a fatty alkyl group containing 12 to 18 carbon atoms and x, y and z total 3 or higher, as well as salts thereof. Generally, cationic agents are preferred for their antiplaque effectiveness.

The antibacterial antiplaque compound is preferably one which has a antibacterial activity such that its phenol coefficient is well over 50, more preferably well above 100, such as above about 200 or more for S. aureus; for instance the phenol coefficient (A.O.A.C.) of benzethonium chloride is given by the manufacturer as 410, for S. aureus. The cationic antibacterial agent will generally be a monomeric (or possibly dimeric) material of molecular weight well below 2,000, such as less than about 1,000. It is, however, within the broader scope of the invention to employ a polymeric cationic antibacterial agent. The cationic antibacterial is preferably supplied in the form of an orally acceptable salt thereof, such as the chloride, bromide, sulfate, alkyl sulfonate such as methyl sulfonate and ethyl sulfonate, phenylsulfonate, such as p-methylphenyl sulfonate, nitrate, acetate, gluconate, etc.

The cationic antibacterial agents and long chain tertiary amine antibacterial agents effectively promote oral hygiene, particularly by removing plaque. However, their use has been observed to lead to staining of dental surfaces or discoloration other than that which occurs from normal contact of dental surfaces with foods, beverages, tobacco etc.

The reason for the formation of such dental stain in the presence of antibacterial antiplaque agent has not been clearly established. Human dental enamel is normally covered by a proteinaceous pellicle derived from saliva protein over which there may be a layer of bacterial plaque. The enamel contains a high proportion (about 95%) of hydroxyapatite which includes $Ca^{+2}$ and $PO_4^{-3}$ ions. In the absence of dental plaque additional $Ca^{+2}$ and $PO_4^{-3}$, particularly from saliva, can be deposited on tooth pellicle on the enamel and such deposits can include color bodies which ultimately stain the tooth as a calcified deposit thereon. It can be that as the cationic or long chain tertiary amine antibacterial agents remove plaque they also denature protein from saliva in the oral environment and the denatured protein can then act as a nucleating agent in which $Ca^{+2}$ and $PO_4^{-3}$ ions are deposited and then crystallized as hydroxyapatite. Small crystals of hydroxyapatite provide a high surface area upon which tooth stain or discoloration is retained.

Previously employed additives which reduced dental staining by cationic antibacterial antiplaque agents also generally reduced the activity of the antibacterial agents or its ability to act on dental plaque to measurable degrees. Further Victamide (e.g., Victamine C) which is the condensation product of ammonia with phosphous pentoxide actually increases staining even in the absence of a cationic antibacterial antiplaque agent and it and other known phosphous containing agents such as disodium-ethane-1-hydroxy-1,1-diphosphonic acid (EHDP) salt precipitate in the presence of antibacterial agent such as bis-biguanido compound, thereby reducing the antiplaque effectiveness of the antibacterial agent.

Moreover, a number of additives have been proposed to retard "natural" discolorations, i.e., the discolorations which occur as a result of contact between the teeth and the usual foods and beverages. Such normal stain has been attributed to ferric and manganeous ions. Accordingly, published German Application 26 13 500 taught the use of chelating agents having relatively high affinity for iron and manganese but relatively low for calcium (a principal component of dental enamel). Preferred chelating agents therein were maltol, kojic acid, ethylene diamine diacetic acid (EDDA) and calcium dihydrogen ethylene diamine tetraacetate (Ca-EDTA) and water-soluble pharmaceutically acceptable salts thereof. However, the chelating activity of such agents or other agents mentioned in that disclosure appears to be unrelated to the ability of an agent to retard dental stain which occurs due to the antibacterial antiplaque agent. Indeed, chelating agents such as maltol and the calcium disodium salt of EDTA are essentially without effect in reducing stain formed in the presence of antibacterial antiplaque agent such as cetyl pyridinium chloride. This may be attributable to the lack of antinucleation properties of chelating agents such as maltol and calcium disodium EDTA.

It is an advantage of this invention that an antinucleating additive is provided which prevents the staining of dental enamel resulting from the use of the cationic or long chain tertiary amine antibacterial agent without substantially adversely affecting antibacterial and antiplaque activity of such agent. Other advantages will be apparent from consideration of the following disclosure.

In accordance with certain of its aspects this invention relates to an oral composition comprising an oral vehicle, a cationic or long chain tertiary amine antibacterial antiplaque agent and a water soluble polyamine polyphosphonic compound of the formula:

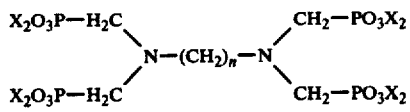

wherein n is a number from 1 to 10 and X is hydrogen or an orally acceptable cation such as alkali metal (e.g., sodium and potassium), ammonium, $C_1$-$C_{18}$ mono-, di- and tri-substituted ammonium (e.g., mono-, di- and triethanolammonium) salts.

Antibacterial agents such are cationic or long chain amine germicides which may be employed in the practice of this invention are described above. They are typically employed in amounts such that the oral product contains between about 0.001% and 15% by weight of the agent. Preferably for desired levels of antiplaque effect, the finished oral product contains about 0.01 to about 5%, and most preferably about 0.025% to 1.0% by weight of the agent. These amounts refer to the quantity of the free base form of the agent.

The stain which generally occurs on dental enamel is unexpectedly prevented when the polyamine polyphosphonic acid or water-soluble salt thereof, is employed. These materials are anti-nucleating agents. In themselves (even in the absence of cationic antiplaque antibacyerial agents) they are effective to reduce formation of dental calculus without unduly decalcifying enamel. However, not all anti-nucleating agents are effective to prevent stain by cationic antibacterial agents are permitting such agents to retain their antiplaque activity. For instance, antiplaque activity of cationic antibacterial agent is substantially reduced in the presence of EHDP.

The polyamine polyphosphonic compounds which are most preferred are ethylenediamine tetra(methylenephosphonic acid), (hereinafter EDITEMPA) and its water-soluble salts, (e.g., sodium, potassium, and ammonium and other pharmaceutically acceptable salts; most preferably the tri-, tetra- or penta-sodium salts). Other polyamine polyphosphonic compounds include: tetramethylenediamine tetra(methylene phosphonic acid), pentamethylene diamine tetra(methylenephosphonic acid), octamethylenediamine tetra (methylene phosphonic acid) and the water-soluble salts of these acids, e.g., sodium, potassium, ammonium and other pharmaceutically acceptable salts. It is noted that EDITEMPA and its water-soluble salts are among the chelating agents disclosed for retarding normal stain formation which may involve iron and manganese. However, as mentioned earlier the stain formed by antibacterial antiplaque agents is quite different in character and origin from the so-called "natural" discolorations which occur as a result of contact between the teeth and the usual foods and beverages.

Mixtures of any of the foregoing polyamine polyphosphonates can be used in the practice of this invention.

The polyamine polyphosphonates and suitable salts thereof can be prepared in any convenient manner, for example, according to the teachings of U.S. Pat. No. 3,928,956 or Moedritzer and Irani, Journal of Organic Chemistry, May 1966, pages 1603-1607.

The concentration of polyamine polyphosphonates in the oral compositions can range widely, typically upward from 0.01% by weight. There is no upper limit on the amount that can be utilized except as dictated by cost or incompatibility with the vehicle. Generally, concentrations from about 0.01% to about 10% by weight are utilized. Oral compositions which in the ordinary course of usage could be accidentally ingested preferably contain lower concentrations of polyamine polyphosphonates. Thus, a mouthwash in accordance with this invention preferably contains less than 3% by weight of polyamine polyphosphonate. Dentifrice compositions, topical solutions and prophylactic pastes, the latter to be administered professionally, can contain from 0.01% to 10% by weight, preferably from 0.1% to 5% by weight of polyaamine polyphosphonate. Most desirably, the polyamine polyphosphate is present in a molar excess to the amount of antibacterial antiplaque agent (based on the free base thereof), in order to best prevent staining by the antibacterial antiplaque agent.

In certain highly preferred forms of the invention the oral composition may be substantially liquid in character, such as a mouthwash or rinse. In such a preparation the vehicle is typically a water-alcohol mixture. Generally, the ratio of water to alcohol is in the range of from about 1:1 to about 20:1 preferably from 3:1 to 20:1 and most preferably about 17:3, by weight. The total amount of water-alcohol mixture in this type of preparation is typically in the range of from about 70% to about 99.9% by weight of the preparation. The pH of such liquid preparations is generally in the range of from about 4.5 to about 9 and typically from about 5.5 to 8. The pH is preferably in the range of from about 6 to about 8.0. It is noteworthy that the composition of the invention permits the use of the polyamine polyphosphate at a pH below 5 without substantially decalcifying dental enamel.

Such liquid oral preparations may also contain a surface active agent and/or a fluorine-providing compound.

In certain other desirable forms of this invention, the oral composition may be substantially solid or pasty in character, such as a toothpowder, a dental tablet or a toothpaste or dental cream. The vehicle of such solid or pasty oral preparations contains polishing material. Examples of polishing materials are water-insoluble sodium metaphosphate, potassium metaphosphate, tricalcium phosphate, dihydrated calcium phosphate, metaphosphate, tricalcium phosphate, dihydrated calcium phosphate, anhydrous dicalcium phosphate, calcium pyrophosphate, magnesium orthophosphate, trimagnesium phosphate, calcium carbonate, alumina, hydrated alumina, aluminum silicate, zirconium silicates, silica, bentonite, and mixtures thereof. Preferred polishing materials include crystalline silica having particle sizes of up to 5 microns, a mean particle size of up to 1.1 microns, and a surface area of up to 50,000 cm$^2$/gm. silica gel, complex amorphorus alkali metal aluminosilicate and hydrated alumina (e.g., alpha-alumina trihydrate).

Alumina, particularly the alpha-alumina trihydrate sold by Alcoa as C333, which has an alumina content of 64.9% by weight, a silica content of 0.008%, a ferric oxide content of 0.003%, and a moisture content of 0.37% at 110° C., and which has a specific gravity of 2.42 and a particle size such that 100% of the particles are less than 50 microns and 84% of the particles are less than 20 microns, is particularly desirable.

When visually clear gels are employed, a polishing agent of colloidal silica, such as those sold under the trademark SYLOID as Syloid 72 and Syloid 74 or under the trademark SANTOCEL as Santocel 100 and alkali metal aluminosilicate complexes are particularly useful, since they have refractive indices close to the refractive indices of gelling agent-liquid (including water and/or humectant) systems commonly used in dentifrices.

Many of the so called "water-insoluble" polishing materials are anionic in character and also include small amounts of soluble material. Thuse, insoluble sodium metaphosphate may be formed in any suitable manner, as illustrated by Thorpe's *Dictionary of Applied Chemistry*, Volume 9, 4th Edition, pp. 510–511. The forms of insoluble sodium metaphosphate known as Madrell salt and Kurrol's salt are further examples of suitable materials. These metaphosphate salts exhibit a minute solubility in water, and therefore are commonly referred to as insoluble metaphosphates. There is present therein a minor amount of soluble phosphate material as impurities, usually a few percent such as up to 4% by weight. The amount of soluble phosphate material, which is believed to include a soluble sodium trimetaphosphate in the case of insoluble sodium metaphosphate, may be reduced by washing with water if desired. The insoluble alkali metal metaphosphate is typically employed in powder form of a particle size such that no more than 1% of the material is larger than 37 microns.

It is further noted that the polyamine polyphosphonate exerts a stabilizing effect on calcium phosphate polishing material as is disclosed in U.S. Pat. No. 3,792,152.

The polishing material is generally present in amounts ranging from about 20% to about 99% by weight of the oral preparation. Preferably, it is present in amounts ranging from about 20% to about 75% in toothpaste, and from about 70% to about 99% in toothpowder.

In the preparation of toothpowders, it is usually suffiient to admix mechanically, e.g., by milling, the various solid ingredients in appropriate quantities and particle sizes.

In pasty oral preparations the combination of the antibacterial antiplaque agent and polyamine polyphosphonic compound should be compatible with the other components of the preparation. Thus, in a toothpaste, the liquid vehicle may comprise water and humect typically in an amount ranging from about 10% to about 90% by weight of the preparation. Glycerine, sorbitol, or polyethylene glycol may also be present as humectants or binders. Particularly advantageous liquid ingredients comprise mixtures of water, glycerine and sorbitol.

In clear gels, where the refractive index is an important consideration, about 3–30% by weight of water, 0 to about 80% by weight of glycerine, and about 20–80% by weight of sorbitol is preferably employed. A gelling agent, such as natural or synthetic gums or gum-like materials, typically Irish moss, sodium carboxymethylcellulose, methyl cellulose, or hydroxyethyl cellulose, may be employed. Other gelling agents which may be employed include gum tragacanth, polyvinylpyrrolidone and starch. They are usually present in toothpaste in an amount up to 10% by weight, preferably in the range of from about 0.5% to about 5%. The preferred gelling agents are methyl cellulose and hydroxyethyl cellulose. In a toothpaste or gel, the liquids and solids are proportioned to form a creamy or gelled mass which is extrudable from a pressurized container or from a collapsible, e.g., aluminum or lead, tube.

The solid or pasty oral preparation which typically has a pH measured on a 20% slurry of about 4.5 to about 9, generally about 5.5 to about 8 and preferably about 6 to about 8.0, may also contain a surface active agent and/or a fluorine-providing compound.

It will be understood that, as is conventional, the oral preparations are to be sold or otherwise distributed in suitably labelled packages. Thus a jar of mouthrinse will have a label describing it, in substance, as a mouthrinse or mouthwash and having directions for its use; and a toothpaste will usually be in a collapsible tube, typically aluminum or lined lead, or other squeeze dispenser for metering out the contents, having a label describing it, in substance, as a toothpaste or dental cream.

In oral compositions such as mouthrinses and toothpastes, a surfactant is often present, e.g. to promote foaming. It will be understood that it is preferable to employ nonionic surfactants rather than their anionic counterparts. Examples of water-soluble nonionic surfactants are condensation products of ethyleneoxide with various compounds reactive therewith having long hydrophobic chain s (e.g. aliphatic chains of 12 to 20 carbon atoms) which condensation products ("ethoxamers") have hydrophilic polyoxyethylene moieties, such as condensation products of ethylene oxide and fatty acids, fatty alcohols, fatty amides, including alcohols such as sorbitan monostearate or polypropyleneoxide (that is Pluronic materials).

In certain forms of this invention a fluorine-providing compound is present in the oral preparation. These compounds may be slightly soluble in water or may be fully water-soluble. They are characterized by their ability to release fluoride ions in water and by substantial freedom from reaction with other compounds of the oral preparation. Among these materials are inorganic fluoride salts, such as soluble alkali metal, alkaline earth metal and heavy metal salts, for example, sodium fluoride, potassium fluoride, ammonium fluoride, lead fluoride, a copper fluoride such as cuprous fluoride, zinc fluoride, a tin fluoride such as stannic fluoride or stannous chlorofluoride, barium fluoride, sodium fluorosilicate, ammonium fluorosilicate, sodium fluorozirconate, sodium monofluorophosphate, aluminum mono- and difluorophosphate. Alkali metal and tin fluorides, such as sodium and stannous fluorides, sodium monofluorophosphate and mixtures thereof, are preferred. A mixture of sodium fluoride and sodium monofluorophosphate is particularly desirable.

The amount of the fluorine-providing compound is dependent to some extent upon the type of compound, its solubility, and the type of oral preparation, but it must be a nontoxic amount. In a solid oral preparation, such as a toothpaste or toothpowder, an amount of such compound which releases a maximum of about 1% by weight of the preparation is considered satisfactory. Any suitable minimum amount of such compound may be used, but it is preferable to employ sufficient compound to release from about 0.005% to 1%, and preferably about 0.1% of fluoride ion. Typically, in the cases of alkali metal fluorides and stannous fluoride, this component is present in an amount up to 2% by weight, based on the weight of the preparation, and preferably in the range of from 0.05% to 1%. In the case of sodium monofluorophosphate, the compound may be present in an amount up to 7.6% by weight, more typically 0.76%. When present in mixture the ratio of sodium monofluorophosphate to sodium fluoride is desirably about 1:1 to 3:1 based on fluorine provided by each.

In a liquid oral preparation such as a mouthwash, the fluorine-providing compound is typically present in an amount sufficient to release up to 0.13%, preferably from 0.0013% to 0.1% and most preferably from 0.0013% to 0.05%, by weight, of fluoride ion.

Various other materials may be incorporated in the oral preparations of this invention. Examples are whitening agents, preservatives, silicones, chlorophyll compounds, and ammoniated material such as urea, diammonium phosphate, monoammonium glycrrhizinate and mixtures thereof. These adjuvants, where present, are incorporated in the preparations in amounts which do not substantially adversely affect the properties and characteristics desired.

Any suitable flavoring or sweetening material may also be employed. Examples of suitable flavoring constituents are flavoring oils, e.g., oils of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, sodium cyclamate, perillartine, and sodium saccharin. Suitably, flavor and sweetening agents may together comprise from 0.01% to 5% or more of the preparations.

Oral preparations of the invention may be prepared by dispersing the cationic antibacterial agent and the polyamine polyphosphonic compound in an oral vehicle which typically includes water.

For instance, a mouthrinse or mouthwash may be prepared by mixing ethanol and water with flavoring oil, nonionic surfactant humectant, cationic antibacterial antiplaque agent, such as benzethonium chloride, cetyl pyridinium chloride or chlorhexidine, sweetener and color and then adding the polyamine polyphosphonic compound, such as EDITEMPA or a water-soluble salt (e.g., tritetra- or penta- sodium salt) thereof and additional water as desired. It is desirable to add the polyamine polyphosphonate after the other ingredients are contacted with each other.

A toothpaste may be prepared by forming a gel with humectant, gum or thickener such as hydroxyethyl cellulose, sweetener and adding thereto polishing agent, flavor, antibacterial agent, such as benzethonium chloride, cetyl pyridinium chloride or chlorhexidine, and additional water, followed by addition of flavoring oil and the polyamine polyphosphonic compound such as EDITEMPA or water-soluble salt thereof. It is preferable to add the polyamine polyphosphonic compound after the other components are contacted with each other. If sodium carboxymethyl cellulose is employed as the gelling agent the procedure of either U.S. Pat. No. 3,842,168 or U.S. Pat. No. 3,843,779, modified by the inclusion of the polyamine polyphosphonic compound is followed.

In the practice of this invention an oral composition such as a mouthwash or toothpaste containing cationic or long chain amine antibacterial antiplaque agent in amount effective to promote oral hygiene and polyamine polyphosphonic compound in amount effective to reduce staining of dental surfaces otherwise resulting from the presence of the antibacterial antiplaque agent is applied regularly to dental enamel, preferably from about 5 times per week to about 3 times daily.

The following specific examples are further illustrative of the nature of the present invention; but it is understood that the invention is not limited thereto. The compositions are prepared in the usual manner and all amounts of the various ingredients are by weight unless otherwise indicated.

EXAMPLE 1

The following mouthwash is prepared by mixing the following ingredients.

|  | Parts |
| --- | --- |
| Flavored alcohol | 15 |
| Pluronic F-108 | 3 |
| Glycerine | 10 |
| Benzethonium chloride | 0.1 |
| Sodium saccharin | 0.03 |

|  | Parts |
|---|---|
| EDITEMPA trisodium salt | 1 |
| Water | Q.S. to 100 |
| pH 8.0 (adjusted with 5 N sodium hydroxide) | |

The several ingredients are mixed with the EDITEMPA trisodium salt and about 10 parts of water being withheld to the end.

The pH of the mouthwash is also adjusted with 5 N sodium hydroxide to prepare additional compositions having pH values of 5.0, 6.6, 6.9, 7.0. With sodium hydroxide, the pH is 4.6. As the pH is adjusted the amount of sodium ion associated with EDITEMPA inherently varies (from 3 to 6).

All compositions are clear without visible evidence of precipitation.

The antiplaque activity and staining levels of the mouthwashes of the same pH and composition except for the absence of the polyamine polyphosphonate salt are determined.

Tests are made of the ability of the compositions to inhibit in vitro plaque formation by allowing plaque to form (for 48 hours at 37° C.) on the surfaces of cleaned and pumiced teeth in a preinoculated sucrose broth containing *Strep mutans*. The pre-grown plaque is then immersed in the test composition and rinsed with a buffer 1–5 times for one minute each. The teeth carrying the plaque are then transferred to a sucrose broth containing 1 mg/100 ml of bromocresol green indicator and incubated at 37° C. anaerobically for 18 hours. An antibacterial compound is considered effective if the indicator does not turn yellow (which begins when pH reaches 5.5) and there is not further growth of the plaque as judged by the increase in turbidity. It is found that on the clean teeth, plaque formation and plaque growth are effectively inhibited.

The tooth staining characteristics of the composition are tested as follows: Stain Test — 250 mgs. bovine albumin (crystallized three times) are added to 2 grams of hydroxy apatite (HAP) powder (Biogel) which serves as a substrate for a stain while the proteins simulate dental pellicle and provide an "amine source." The mouthrinse is added to the mixture followed by a 7.5% of buffered acetaldehyde which serves as a carbonyl source. The mixture is shaken at 37° C. for 18 hours. The stained HAP is separated from the solution via filteration and dried at 37° C. The color on the powder is read on Gardner color difference meter.

Color levels are determined on a Gardner Color Difference Meter before and after the test composition is applied to the colored material.

The antiplaque results reveal that with and without EDITEMPA salt at each of pH 8.0, 7.0, 6.9, 6.6, 5.0, and 4.6, the rinse is active after 5 rinses with buffer and 3 day plaque growth and acid production are inhibited.

Thus, it is observed that EDITEMPA does not reduce the in vitro antiplaque activity of benzethonium chloride.

The antistain results are as follows with the mouthwashes at pH 4.9, 7.0 and 8.0 (these mouthwashes were at pH 5.0, 7.0 and 8.0 before applying to the in vitro stain):

| Composition pH | EDITEMPA sodium salt Presence | Reflectance | Reflectance Difference |
|---|---|---|---|
| Control- 5.0 to 8.0 | No EDITEMPA sodium salt and no Benzethonium Chloride | 38.5 | |
| 5.0 | Yes | 33.9 | 1.1 |
| 5.0 | No | 32.8 | |
| 7.0 | Yes | 39.8 | 5.9 |
| 7.0 | No | 33.9 | |
| 8.0 | Yes | 40.4 | 7.0 |
| 8.0 | No | 33.4 | |

Thus, it is observed the EDITEMPA sodium salt substantially reduces staining by benzethonium chloride particularly at pH 7.0 and 8.0 and also to a noted degree at pH 5.0.

Similar antiplaque and antistain results are observed with corresponding mouthwashes containing 0.05 to 0.1% sodium salt at pH of 4.8 to 8.0. In mouthwashes of the same formulation at pH 7 containing 1% cetyl pyridinium chloride and 0.6, 0.9 and 1%, EDITEMPA sodium salt, the cetyl pyridinium chloride remains active and the stain resulting therefrom is reduced by 12-13 reflectance units.

EXAMPLE 2

Mouthwashes similar to those of Example 1 are prepared except that chlorhexidine diacetate and chlorhexidine digluconate in amount corresponding to 0.1 part of chlorhexidine free base and 0.1 part of EDITEMPA sodium salt are present. The pH of the mouthwashes without sodium hydroxide adjustment is 5.0 (EDITEMPA being present as the tetra-sodium salt). These mouthwashes are active against plaque in vitro after four rinses with the buffer and inhibit plaque growth and acid as do the corresponding mouthwashes without EDITEMPA. In the antistain test the stain level caused when 0.1 part of EDITEMPA is present is less than the stain level when it is absent. Similar reductions are observed when 0.05 to 1 part of EDITEMPA are used with the pH being from 5.0 to 7.0.

Alexidine also maintains its antiplaque effect with reduced staining in the presence of EDITEMPA, as do other antibacterial antiplaque agents including cetyl pyridinium chloride and a $C_{12}$-$C_{18}$ alkyl tertiary amine of the formula:

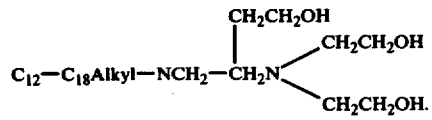

When EDITEMPA is replaced by other polyamine polyphosphonates including tetramethylene diamine tetra(methylene phosphonic acid), pentamethylene diamine tetra(methylene phosphonic acid), hexamethylenediamine tetra(methylene phosphonic acid) and octamethylenediamine tetra(methylene phosphonic acid) similar desirable results are obtained.

On the other hand, other antinucleating agents including Victamide, ethane-1-hydroxy-1,1-diphosphonic acid disodium salt and 8-hydroxyquinoline precipitate in the presence of the antibacterial antiplaque agent and reduce its antiplaque effectiveness. Moreover, Victamide actually increases staining.

EXAMPLE 3

The following mouthrinse is prepared with EDI-TEMPA and a portion of the water added last:

|  | Parts |
|---|---|
| Ethanol | 5 |
| Flavor | 0.073 |
| Pluronic F-108 | 3 |
| Glycerine | 10 |
| Sodium saccharin | 0.03 |
| Benzethonium chloride | 0.075 |
| EDITEMPA - trisodium salt | 0.75 |
| Water | Q.S. to 100 |
| pH-8.0 (adjusted with 5 N sodium hydroxide) | |

This mouthwash, a placebo without benzethonium chloride and EDITEMPA and a control without EDI-TEMPA are applied to the teeth of beagles which are first subjected to dental prophylaxis to remove existing soft and hard dental deposits. A disclosing solution is used to insure complete removal. Three groups of five beagles each are subjected to gentle oral sprays twice a day, 5 days a week, for two weeks with the mouthrinses. Plaque is evaluated after spraying the teeth with disclosing solution. The results are:

| Group | Mean Plaque | % Reduction |
|---|---|---|
| Placebo | 1.7 | |
| 0.075 Benzethonium chloride | 1.2 | 29 |
| 0.075 Benzethonium chloride & 0.75 EDITEMPA | 1.3 | 28 |

Thus, plaque is reduced to essentially the same degree when EDITEMPA is present as when it is not. The same mouthrinse is applied to humans, as is the mouthrinse without EDITEMPA, to groups of 20 each following dental prophylaxis. Rinsing is twice a day under supervision, 7 days a week for 6 weeks. The results is plaque reduction and stain reduction are as follows:

| Group | Mean Plaque | Stain Quotient |
|---|---|---|
| 0.075% Benzethonium Chloride | 1.685 | 0.1287 |
| 0.075% Benzethonium Chloride & 0.75% EDITEMPA | 1.824 | 0.0851 |

Thus, the quantity of plaque formation is comparable in both groups while the amount of stain developed when EDITEMPA is present is substantially less (33.9%).

While the stain level in both cases is higher than the stain formed naturally in vivo in the absence of benzethonium chloride, the presence of the EDITEMPA substantially reduces the stain level resulting from the presence of benzethonium chloride. Similar results are obtained after 12 weeks.

Similar desirable reductions in stain are present when chlorhexidine and cetyl pyridinium chloride replaces benzethonium chloride.

EXAMPLE 4

The following toothpastes with reduced staining from antiplaque agent:

| | PARTS | | | | |
|---|---|---|---|---|---|
| | A | B | C | D | E |
| Hydrated alumina | 30 | 30 | 42 | 42 | 42 |
| Anhydrous alumina | — | — | 10 | 10 | 10 |
| Glycerine | 16 | 16 | 26 | 22 | 22 |
| Sorbitol (70%) | 6 | 6 | — | — | — |
| Pluronic F-108 | 3 | 3 | — | — | — |
| Polyoxyethylene (20) sorbitan monoisostearate | — | — | 1 | 1 | 1 |
| Hydroxyethyl cellulose | 1.2 | 1.2 | 1.3 | 1.3 | 1.3 |
| Benzethonium chloride | 0.5 | — | — | 0.5 | — |
| Chlorhexidine digluconate (20%) | — | 4.725 | — | — | — |
| Cetyl pyridinium chloride | — | — | 0.75 | — | 0.75 |
| EDITEMPA (as acid) | 1.69 | 1.69 | 1.69 | 1.69 | 1.69 |
| Monoammonium glycyrrhizinate | — | — | — | 0.1 | 0.1 |
| Sodium saccharin | 0.17 | 0.17 | 0.2 | 0.2 | 0.2 |
| Sodium fluoride | — | — | — | — | 0.11 |
| Sodium monofluorophosphate | — | — | 0.76 | — | 0.76 |
| Flavor | 0.8 | 0.8 | 1 | 1 | 1 |
| Water and Sodium Hydroxide to pH 7 (20% slurry) | Q.S. to 100 | Q.S. to 100 | Q.S. to 100 | Q.S. to 100 | Q.S. to 100 |

It will be apparent to one skilled in the art that modifications of the above examples may be made thereto.

We claim:

1. An oral composition comprising an oral vehicle, a quaternary ammonium antibacterial antiplaque agent tending to cause staining of dental surfaces and antibacterial agent being present in amount which provides about 0.001% to about 15% by weight based on the free base form thereof and an amount of at least about 0.01% by weight of a water soluble polyamine polyphosphonic compound stain reducing agent, which amount of at least about 0.01% by weight is such that upon ingestion an adverse effect does not occur, said polyamine polyphosphonic having the formula:

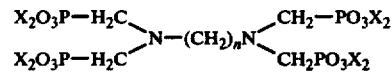

wherein n is a number from 1 to 10 and X is selected from the group consisting of hydrogen and an orally acceptable cation and said polyamine polyphosphonic compound reduces stain formed by said antibacterial antiplaque agent.

2. The oral composition of claim 1 wherein said polyamine polyphosphonic compound is present in amount of about 0.01% to about 10% by weight.

3. The oral composition of claim 1 wherein said antibacterial antiplaque agent is present in amount of about 0.01% to about 5% by weight based on the free base form of said agent and said polyamine polyphosphonic acid is present in a molar excess to said agent.

4. The oral composition of claim 1 wherein said antibacterial antiplaque agent is benzethonium chloride.

5. The oral composition of claim 1 wherein said antibacterial antiplaque agent is a quaternary ammonium compound containing 1 to 2 alkyl groups of 8 to 20 carbon atoms.

6. The oral composition of claim 5 wherein said antibacterial antiplaque agent is cetyl pyridinium chloride.

7. The oral composition of claim 1 wherein said polyamine polyphosphonic compound has the formula:

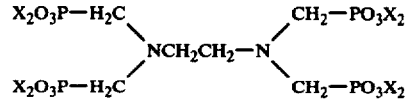

wherein X is selected from the group consisting of an orally acceptable cation and hydrogen.

8. The oral composition of claim 7 wherein said compound is the tri-, tetra- or penta- sodium salt.

9. The oral composition of claim 1 wherein said vehicle is an aqueous-alcohol and said composition is a mouthwash of pH of about 4.5 to about 9.

10. The oral composition of claim 1 wherein said vehicle comprises a liquid vehicle and a gelling agent and a dentally acceptable polishing material is present and said composition is a toothpaste of pH of about 4.5 to about 9.

11. The oral composition of claim 10 wherein said polishing material is hydrated alumina.

12. The oral composition of claim 11 wherein at least one fluorine-providing compound is present in amount sufficient to release about 0.005% to 1% by weight of fluorine.

13. The oral composition of claim 12 wherein sodium fluoride and sodium monofluorophosphate are present.

14. A mouthwash comprising an aqueous-alcohol vehicle, about 0.01% to about 5.0% based on its free base weight of benzethonium chloride which tends to cause staining of dental surfaces and about 0.1% to about 5% by weight of a polyamine polyphosphonic compound stain reducing agent of the formula:

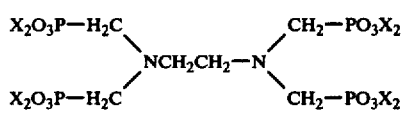

wherein X is selected from the group consisting of hydrogen and an orally acceptable cation, the amount said polyamine polyphosphonic compound being in molar excess to the amount of the free based of benzethonium chloride, said polyamine polyphosphonic compound reducing stain formed by said benzethonium chloride.

15. A mouthwash comprising an aqueous-alcohol vehicle, about 0.01% to about 5.0% based on its free base weight of cetyl pyridinium chloride and about 0.1% to about 5% by weight of a polyamine polyphosphonic compound of the formula:

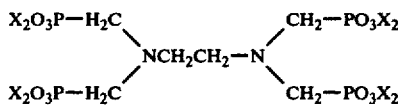

wherein X is selected from the group consisting of hydrogen and an orally acceptable cation, the amount said polyamine polyphosphonic compound being in molar excess to the amount of the free based of cetyl pyridinum chloride, said polyamine polyphosphonic compound reducing stain formed by said cetyl pryidinium chloride.

16. A mouthwash comprising an aqueous-alcohol vehicle, about 0.01% to about 5% based on its free base weight of a water-soluble pharmaceutically suitable salt of chlorhexidine which tends to cause staining of dental surfaces and about 0.1% to about 5% by weight of a polyamine polyphosphonic compound stain reducing agent of the formula:

wherein X is selected from the group consisting of hydrogen and an orally acceptable cation, the amount of said polyamine polyphosphonic compound being in molar excess to the free base amount of chlorhexidine, said polyamine polyphosphonic compound reducing stain formed by said chlorhexidine.

17. A method of preparing an oral composition comprising an oral vehicle, a quaternary ammonium antibacterial antiplaque agent tending to cause staining of dental surfaces, said antibacterial agent being present in amount which provides about 0.001% to about 15% by weight based on the free base form thereof and an amount of at least about 0.01% by weight of a water soluble polyamine polyphosphonic compound stain reducing agent, which amount of at least about 0.01% by weight is such that upon ingestion an adverse effect does not occur, said polyamine polyphosphonic compound having the formula:

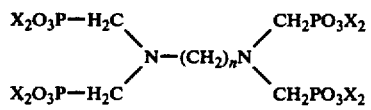

wherein n is a number from 1 to 10 and X is selected from the group consisting of hydrogen and an orally acceptable cation, wherein said polyamine polyphosphonic compound is added to the remaining components of said composition after said components have been contacted with each other wherein said polyamine compound reduces the stain formed by said antibacterial antiplaque agent.

18. A method of improving oral hygiene comprising applying to the oral cavity an oral composition an oral vehicle, a quaternary ammonium antibacterial antiplaque agent tending to cause staining of dental surfaces, said antibacterial agent being present in amount which provides about 0.001% to about 15% by weight based on the free based form thereof and an amount at least about 0.01% by weight of a water soluble polyamine polyphosphonic compound stain reducing agent, which amount of at least about 0.01% by weight is such that upon ingestion an adverse effect does not occur, said polyamine polyphosphonic compound having the formula:

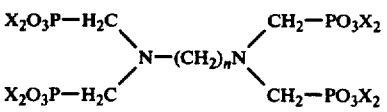

wherein n is a number from 1 to 10 and X is selected from the group consisting of hydrogen and an orally acceptable cation, wherein said polyamine polyphosphonic compound reduces stain formed by said antibacterial antiplaque agent.

19. An oral composition comprising an oral vehicle an amidine antibacterial antiplaque agent tending to cause staining of dental surfaces in amount which provides about 0.001% to about 15% by weight of the free base thereof and an amount of at least about 0.01% by weight of a water soluble polyamine polyphosphonic compound stain reducing agent, which amount of at least about 0.01% is such that upon ingestion an adverse effect does not occur, said polyamine polyphosphonic compound having the formula:

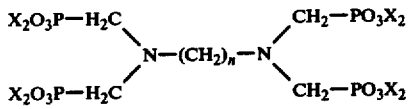

wherein n is a number from 1 to 10 and X is selected from the group consisting of hydrogen and an orally acceptable cation, and said polyamine polyphosphonic compound reduces the stain formed by said antibacterial antiplaque agent.

20. The oral composition of claim 19 wherein said antibacterial antiplaque agent is a substituted guanidine.

21. The oral composition of claim 20 wherein said antibacterial antiplaque agent is a pharmaceutically acceptable water soluble salt of an agent selected from the group consisting of chlorhexidine and alexidine.

22. The oral composition of claim 21 wherein said antibacterial antiplaque agent is a pharmaceutically acceptable water soluble salt of chlorhexidine.

23. An oral composition comprising an oral vehicle, about 0.001% to about 15% by weight of a long chain amine antibacterial agent tending to cause stain of dental surfaces containing a fatty alkyl group of 12 to 18 carbon atoms, and an amount of at least about 0.01% by weight of a water soluble polyamine polyphosphonic compound stain reducing agent, which amount of at least about 0.01% is such that upon ingestion an adverse effect does not occur, said polyamine polyphosphonic compound having the formula:

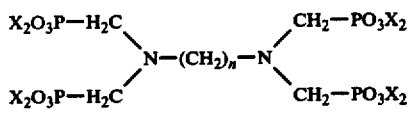

wherein n is a number from 1 to 10 and X is selected from the group consisting of hydrogen and an orally acceptable cation, and said polyamine polyphosphonic compound reduces the stain formed by said antibacterial antiplaque agent.

* * * * *